US012544057B2

(12) United States Patent
Dong

(10) Patent No.: US 12,544,057 B2
(45) Date of Patent: Feb. 10, 2026

(54) ALL-SUTURE ANCHOR AND IMPLANTABLE DEVICE

(71) Applicant: Star Sports Medicine Co., Ltd., Beijing (CN)

(72) Inventor: Wenxing Dong, Beijing (CN)

(73) Assignee: Star Sports Medicine Co., Ltd., Beijing (CN)

( * ) Notice: Subject to any disclaimer, the term of this patent is extended or adjusted under 35 U.S.C. 154(b) by 357 days.

(21) Appl. No.: 18/030,082

(22) PCT Filed: Jan. 6, 2023

(86) PCT No.: PCT/CN2023/070846
§ 371 (c)(1),
(2) Date: Apr. 4, 2023

(87) PCT Pub. No.: WO2023/134556
PCT Pub. Date: Jul. 20, 2023

(65) Prior Publication Data

US 2025/0082321 A1 Mar. 13, 2025

(30) Foreign Application Priority Data

Jan. 13, 2022 (CN) ......................... 202210034576.4

(51) Int. Cl.
*A61B 17/04* (2006.01)

(52) U.S. Cl.
CPC .. *A61B 17/0401* (2013.01); *A61B 2017/0409* (2013.01)

(58) Field of Classification Search
CPC ........ A61B 17/0401; A61B 2017/0403; A61B 2017/0404; A61B 2017/0406; A61B 2017/0408; A61B 2017/0409; A61B 2017/0414; A61B 2017/042; A61B 2017/0445
See application file for complete search history.

(56) References Cited

U.S. PATENT DOCUMENTS

| | | | | |
|---|---|---|---|---|
| 6,511,498 | B1 * | 1/2003 | Fumex | A61B 17/0401 606/232 |
| 9,119,893 | B2 * | 9/2015 | McDevitt | A61B 17/0401 |
| 9,320,512 | B2 * | 4/2016 | Dooney, Jr. | A61F 2/0811 |
| 10,499,901 | B2 * | 12/2019 | Nason | A61B 17/0401 |
| 12,262,885 | B2 * | 4/2025 | Qi | A61B 17/0482 |

(Continued)

*Primary Examiner* — Dianne Dornbusch
(74) *Attorney, Agent, or Firm* — Bay State IP, LLC

(57) ABSTRACT

The present disclosure provides an all-suture anchor which includes a suture cannula, a pulling wire, an outer tube and an inserter, wherein the suture cannula is provided in the outer tube, the pulling wire goes through the suture cannula, the pulling wire wraps around the inserter, the suture cannula and the outer tube are both in plug-in fit with the inserter, both ends of the pulling wire pass through the suture cannula, respectively, and pass out of one end of the outer tube far from the suture cannula, the inserter is configured to push the suture cannula out of the outer tube, and the pulling wire is configured to pull the suture cannula pushed out of the outer tube, so that the suture cannula retracts, stacks and expands. The expanded suture cannula clings to the side wall of a bone tunnel to provide a fulcrum for fixing the anchor.

9 Claims, 5 Drawing Sheets

(56) References Cited

U.S. PATENT DOCUMENTS

| | | | | |
|---|---|---|---|---|
| 2006/0276871 | A1* | 12/2006 | Lamson | A61B 17/0482<br>606/232 |
| 2011/0022084 | A1* | 1/2011 | Sengun | A61B 17/0401<br>606/228 |
| 2011/0098727 | A1* | 4/2011 | Kaiser | A61B 17/0401<br>606/228 |
| 2012/0197271 | A1* | 8/2012 | Astorino | A61B 17/06166<br>606/232 |
| 2013/0123810 | A1* | 5/2013 | Brown | A61B 17/04<br>606/144 |
| 2013/0131722 | A1* | 5/2013 | Marchand | A61B 17/0401<br>606/232 |
| 2019/0247039 | A1* | 8/2019 | Gregoire | A61F 2/0811 |

* cited by examiner

ALL-SUTURE ANCHOR AND IMPLANTABLE DEVICE

CROSS REFERENCE TO RELATED APPLICATION

This application is for entry into the U.S. National Phase from which priority is claimed under all applicable sections of Title 35 of the United States Code including, but not limited to, Sections 120, 363, and 365(c) to International Application No. PCT/CN2023/070846 filed on Jan. 6, 2023, and which in turn claims priority under 35 USC 119 to Chinese Patent Application No. 202210034576.4 filed on Jan. 13, 2022.

TECHNICAL FIELD

The present disclosure relates to the technical field of medical devices, in particular to an all-suture anchor and an implantable device.

BACKGROUND

An all-suture anchor in joint surgery and sports medicine is a bone anchor implant, which deforms the anchor by the displacement of a pulling wire, expands in the bone and squeezes the surrounding tissues, so as to obtain a fixed point. It is convenient for doctors to carry out subsequent tissue suture.

The structure of an all-suture anchor can be classified into two types, a single-head cylindrical type and a double-folded type. A single-head cylindrical anchor, whose shape is a simple cylinder, is implanted into a bone tunnel by means of an insertion structure. The insertion structure is the overlapping of two stainless steel tubes, which are referred to as an inner tube and an outer tube. Before implantation, the anchor stays in the hole of the inner tube. During implantation, the inner tube retreats, leaves the anchor in the bone tunnel, and then tightens the pulling wire to complete the implantation. The advantage of the single-head cylindrical anchor is that the implanting and knotting action is stable. The double-folded all-suture anchor has the structure of alternating between a pulling wire and an anchor nail body, which is generally inserted into the bone tunnel in the double-folding form and can be fixed without inner and outer tubes. The advantages are simple in structure and fast in implantation speed.

Although the knotting action of the single-head cylindrical anchor is stable and reliable during implantation, the design of the insertion structure of the inner and outer tubes makes the implantation action complicated. The distal end of the tubes needs to be connected with a complex transmission mechanism to realize the alternating action of the inner and outer tubes. The cost of the implant is high. The main defect of the double-folded all-suture anchor lies in its stability, which relies on the friction between the double-folded all-suture anchor and the inner wall of the bone tunnel to form a fulcrum, and relies on the friction force to assist in forming knots. Because of the individual differences in friction force, the force fluctuates up and down with the difference of bone structures, surgical methods and surgical tools, so that the fixing performance of the double-folded all-suture anchor is unstable, and there is a certain chance of direct detachment. Therefore, it is necessary to design an anchor with simple operation and high stability to solve the existing problems.

SUMMARY

In order to overcome the shortcomings in the prior art, the present disclosure provides an all-suture anchor and an implantable device.

In order to achieve the above purpose, in a first aspect, the all-suture anchor according to the present disclosure comprises: a suture cannula, a pulling wire, an outer tube and an inserter, wherein the suture cannula is provided in the outer tube, the pulling wire goes through the suture cannula, the pulling wire wraps around the inserter, the suture cannula and the outer tube are both in plug-in fit with the inserter, both ends of the pulling wire pass through the suture cannula, respectively, and pass out of one end of the outer tube far from the suture cannula, the inserter is configured to push the suture cannula out of the outer tube, and the pulling wire is configured to pull the suture cannula pushed out of the outer tube, so that the suture cannula retracts, stacks and expands.

Combined with the first aspect, in a possible embodiment, the head end of the suture cannula retracts into the suture cannula, the side of the retracted head end of the suture cannula is provided with a first wire passing hole, and the pulling wire penetrates into the first wire passing hole.

Combined with the first aspect, in a possible embodiment, two second wire passing holes and two third wire passing holes are symmetrically provided at the side of the suture cannula, the third wire passing hole is located at the side of the second wire passing hole close to the outer tube, and the pulling wire in the suture cannula is capable of passing out of the suture cannula from the second wire passing hole, and then penetrates into the suture cannula from the corresponding third wire passing hole.

Combined with the first aspect, in a possible embodiment, the suture cannula has a hollow woven structure.

Combined with the first aspect, in a possible embodiment, the suture cannula is in interference fit with the inner wall of the outer tube.

Combined with the first aspect, in a possible embodiment, the inserter is provided with a shoulder-shaped sinking platform, and the shoulder-shaped sinking platform is configured to be in contact with the tail of the suture cannula to limit the detachment of the suture cannula.

Combined with the first aspect, in a possible embodiment, the outer tube and the inserter are made of SUS304 medical stainless steel.

Combined with the first aspect, in a possible embodiment, the ends of the outer tube and the inserter far from the suture cannula are both connected with the same handle, the through hole goes through the inside of the handle, and the outer surface of the outer tube is fixedly connected with the side of the through hole.

Combined with the first aspect, in a possible embodiment, the inserter goes through the handle through the through hole, a pulley is mounted at the side of the inserter located in the handle, a chute is provided in the handle, and the pulley is only movable along the chute in the handle.

In a second aspect, there is provided an implantable device, comprising the all-suture anchor described above.

The embodiment of the present disclosure has the following advantages.

Compared with the prior art, the all-suture anchor according to the present disclosure pushes out the suture cannula in the outer tube through the inserter, and then pulls the end of the suture cannula to retract through the pulling wire, so that the end of the suture cannula expands due to retraction and stacking, and the expanded suture cannula is blocked in the bone tunnel through the outer tube. The expanded suture cannula clings to the side wall of the bone tunnel to provide a fulcrum for fixing the anchor, which increases the axial pull-out resistance of the anchor, improves the stability and the success rate of knotting of the anchor. At the same time, the operation is simple and convenient, which eliminates the alternate linkage of the inner and outer tube nail planting structures.

In order to make the above objects, features and advantages of the present disclosure more obvious and understandable, the following preferred embodiments will be described in detail with reference to the attached drawings.

BRIEF DESCRIPTION OF THE DRAWINGS

In order to explain the technical scheme of the embodiments of the present disclosure more clearly, the drawings that need to be used in the embodiments will be briefly introduced hereinafter. It should be understood that the following drawings only show some embodiments of the present disclosure, so as not to be regarded as limiting the scope. For those skilled in the art, other relevant drawings can be obtained according to these drawings without any creative labor.

DESCRIPTION OF REFERENCE NUMERALS OF MAIN COMPONENTS

Figure 1:
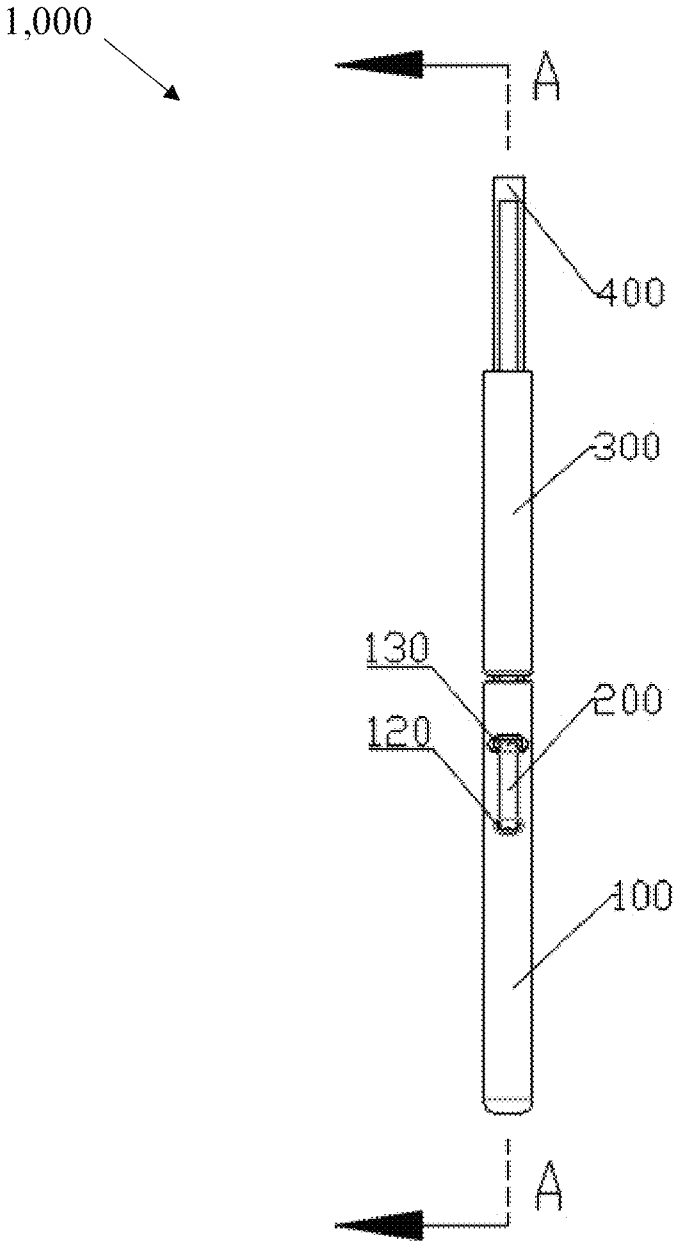
FIG. 1 shows a schematic structural diagram of an anchor.

100—suture cannula, 110—first wire passing hole, 120—second wire passing hole, 130—third wire passing hole, 200—pulling wire, 300—outer tube, 400—inserter, 410—shoulder-shaped sinking platform, 500—handle, 510—through hole, 520—pulley, 530—chute.

DETAILED DESCRIPTION OF THE EMBODIMENTS

Embodiments of the present disclosure will be described in detail hereinafter. Examples of the embodiments are shown in the accompanying drawings, in which the same or similar reference numerals refer to the same or similar elements or elements with the same or similar functions throughout. The embodiments described with reference to the accompanying drawings hereinafter are exemplary, which are only used for explaining the present disclosure, and should not be construed as limiting the present disclosure.

In the description of the present disclosure, it should be understood that the orientational or positional relationships indicated by the terms such as "center", "longitudinal", "transverse", "length", "width", "thickness", "up", "down", "front", "back", "left", "right", "vertical", "horizontal", "top", "bottom", "inside", "outside", "clockwise", "counter-clockwise", "axial", "radial", "circumferential" are based on the orientational or positional relationships shown in the drawings only for the convenience of describing the present disclosure and simplifying the description, rather than indicate or imply that the referred devices or elements must have a specific orientation, be constructed and operated in a specific orientation, and therefore should not be construed as limiting the present disclosure.

In addition, the terms such as "first" and "second" are only used for the purpose of description, and cannot be understood as indicating or implying relative importance or implicitly indicating the number of indicated technical features. Therefore, the features defined with "first" and "second" can include one or more of these features explicitly or implicitly. In the description of the present disclosure, "a plurality of" means two or more, unless otherwise specifically defined.

In the present disclosure, unless otherwise specified and defined expressly, the terms such as "mount", "link", "connect" and "fix" should be understood broadly, for example, it can be fixed connection, detachable connection or integral connection; or mechanical connection or electrical connection; or direct connection or indirect connection through an intermediate medium, or internal communication in two elements or interaction between two elements. For those skilled in the art, the specific meanings of the above terms in the present disclosure can be understood according to specific situations.

In the present disclosure, unless otherwise specified and defined, the first feature "above" or "below" the second feature may be the direct contact between the first feature and the second feature, or the indirect contact between the first feature and the second feature through an intermediate medium. Further, the first feature is "on", "above" and "over" the second feature, indicating that the first feature is directly above or obliquely above the second feature, or only indicating that the horizontal height of the first feature is higher than that of the second feature. The first feature is "below", "under" and "underneath" the second feature, indicating that the first feature is directly under or obliquely under the second feature, or only indicating that the horizontal height of the first feature is smaller than that of the second feature.

Embodiment 1

Referring to FIG. 1, the present disclosure provides an all-suture anchor, which comprises a suture cannula 100, a pulling wire 200, an outer tube 300 and an inserter 400. The suture cannula 100 is provided in the outer tube 300. The pulling wire 200 goes through the suture cannula 100. The pulling wire 200 wraps around the inserter 400. The suture cannula 100 and the outer tube 300 are in plug-in fit with the inserter 400. The suture cannula 100 and the outer tube 300 are both in plug-in fit with the inserter 400. The end of the pulling wire 200 passes through the inside of the suture cannula 100 and is located at the outer end of the outer tube 300. The inserter 400 is configured to push the suture cannula 100 out of the outer tube 300. The pulling wire 200 is configured to pull the suture cannula 100 to retract, stack and expand.

In this embodiment, the suture cannula 100 stays inside the outer tube 300 before use. The suture cannula 100 is in interference fit with the outer tube 300 and the inserter 400. The suture cannula 100 wraps around the inserter 400. The outer tube 300 tightly compresses the suture cannula 100 on its inner surface. The suture cannula 100 is squeezed and deformed by the inserter 400 to store energy. When the suture cannula 100 starts to be used, the inserter 400 is pushed to move into the outer tube 300. The end of the inserter 400 pushes the suture cannula 100 out of the outer tube 300. The suture cannula 100 is no longer restricted by the outer tube 300, releases energy and begins to deform and expand.

Figure 2:
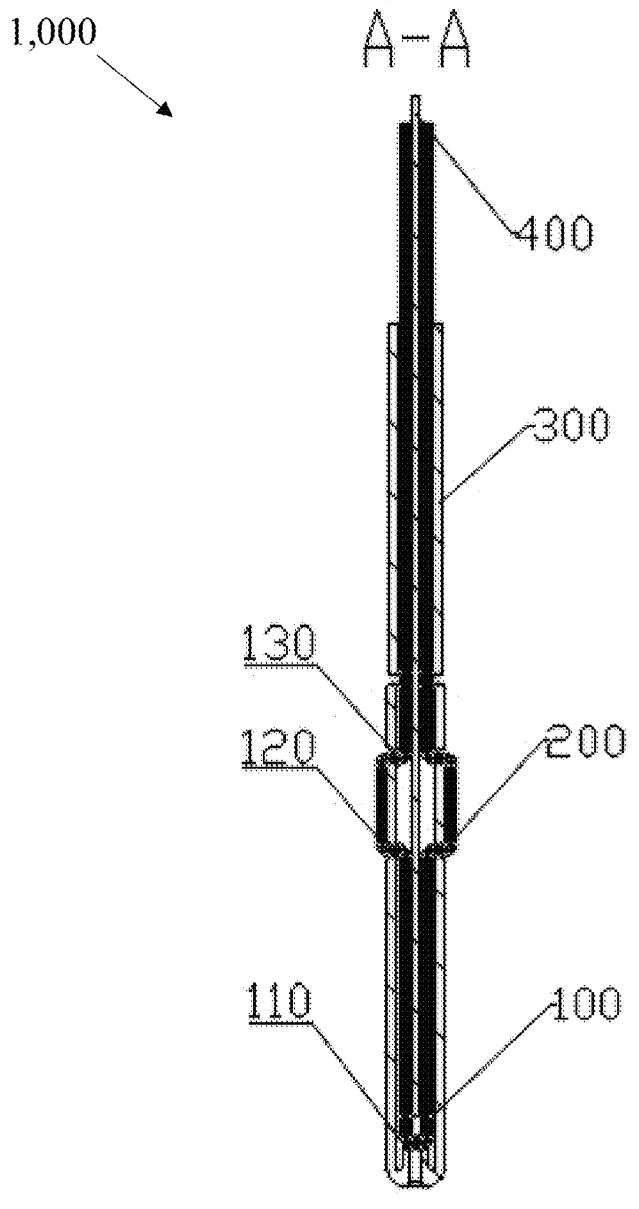
FIG. 2 shows a cross-sectional diagram along line A-A of FIG. 1.

Referring to FIG. 2, when the suture cannula 100 is completely pushed out of the outer tube 300, the deformation of the suture cannula 100 ends, and the diameter of the suture cannula 100 is approximately the same as that of the outer tube 300. At this time, the connection relationship among the suture cannula 100, the inserter 400 and the outer tube 300 changes. The suture cannula 100 is tightly wrapped at the head end of the inserter 400, and they are tightly fit. The inserter 400 is provided with a shoulder-shaped sinking platform 410, which is in contact with the tail of the suture cannula 100 to limit the backward movement of the suture cannula 100.

In this embodiment, the suture cannula 100 and the pulling wire 200 are assembled together, and they are made of ultra-high molecular weight polyethylene fibers knitted by a ribbon knitting machine. The suture cannula 100 is a hollow woven bag with a certain thickness. Therefore, the suture cannula 100 can be in interference fit with the inner wall of the outer tube 300 before the anchor is implanted, and the suture cannula 100 with a hollow structure can be retracted from the head end better. The function of the suture cannula 100 is to closely cling to the side of bone tissues through deformation and expansion, thus providing a fulcrum for fixing the anchor. The function of the pulling wire 200 is to force the suture cannula 100 to deform and expand, while the distal end of the suture can be connected with soft tissues.

In this embodiment, the outer tube 300 and the inserter 400 are functional structures responsible for implantation and assisting in forming knots, both of which are forged from SUS304 medical stainless steel, and are processed into a specified size and shape by laser or wire cutting.

In this embodiment, the pulling wire 200 and the suture cannula 100 form a complete all-suture anchor, but the assistance of the inserter 400 and the outer tube 300 is required for forming knots. The inserter 400 is clamped inside the suture cannula 100. The function of the inserter 400 is to provide rigid support for the flexible suture cannula 100 when the anchor is implanted, so as to prevent the suture cannula 100 from being deformed in advance or being unable to detach from the implanted structure due to its soft material. The outer tube 300 restricts the movement of the tail of the suture cannula 100 after the suture cannula 100 enters the bone tunnel, ensuring that the suture cannula 100 completely expands inside the bone tunnel.

In this embodiment, the inserter 400 is a plate inserter. The cooperation between the outer tube 300 and the inserter 400 forms a new nail implanter, which is different from the traditional double-tube nail implanter in principle and structure movement process. The traditional nail implanter consists of a metal inner tube and a metal outer tube. The metal outer tube covers the metal inner tube, the metal inner tube contains an anchor, and there is sliding friction between the metal inner tube and the metal outer tube. When in use, the metal inner tube is first pulled to move backward. After the anchor is completely exposed, the metal inner tube stops moving, and then the pulling wire 200 is pulled. The tail of the anchor is limited by the metal inner tube and the metal outer tube. The anchor converts mechanical energy into deformation energy. After the expansion and deformation of the anchor, the implanting action is completed. Compared with the traditional nail implanter, the device can achieve the purpose through a simpler structure.

Figure 3:
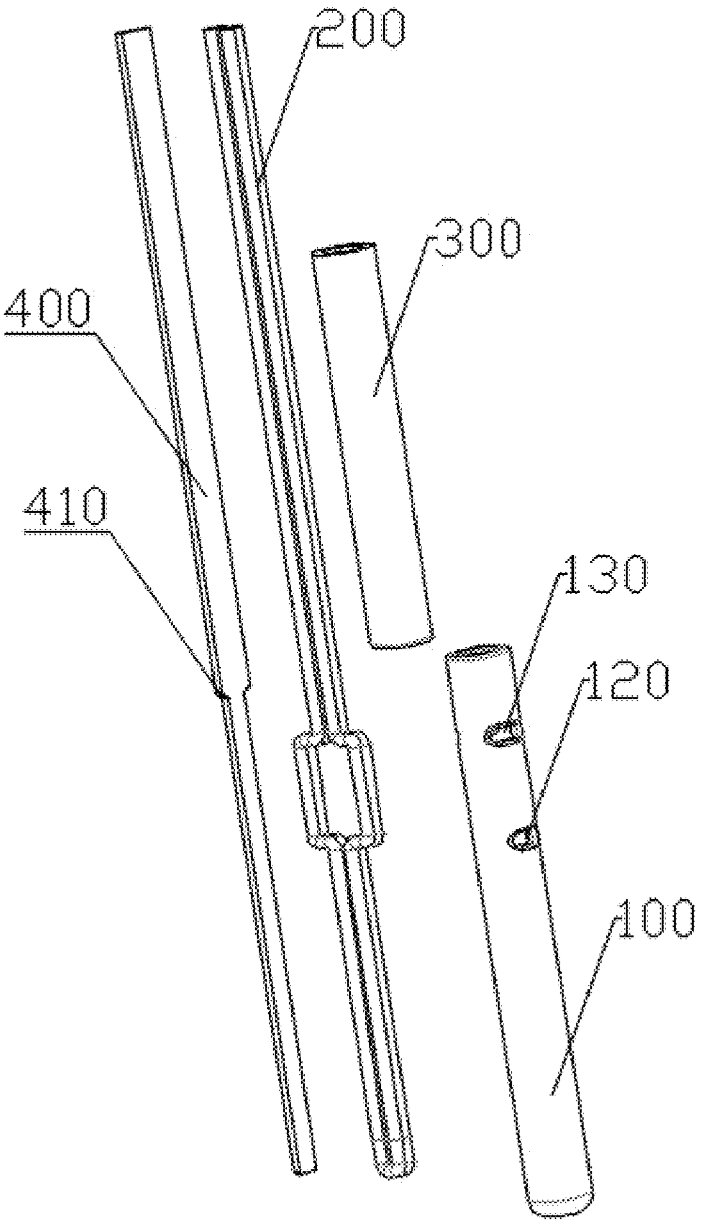
FIG. 3 shows an explosion diagram of FIG. 1.
Figure 4:
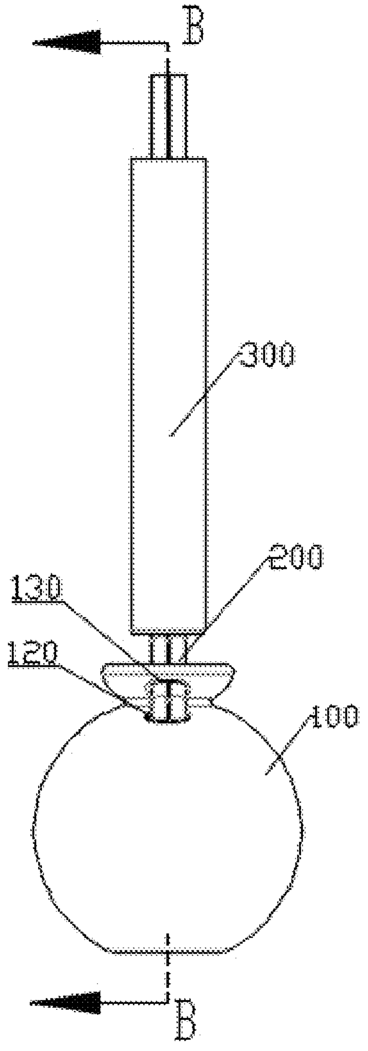
FIG. 4 shows a use state diagram of an anchor.
Figure 5:
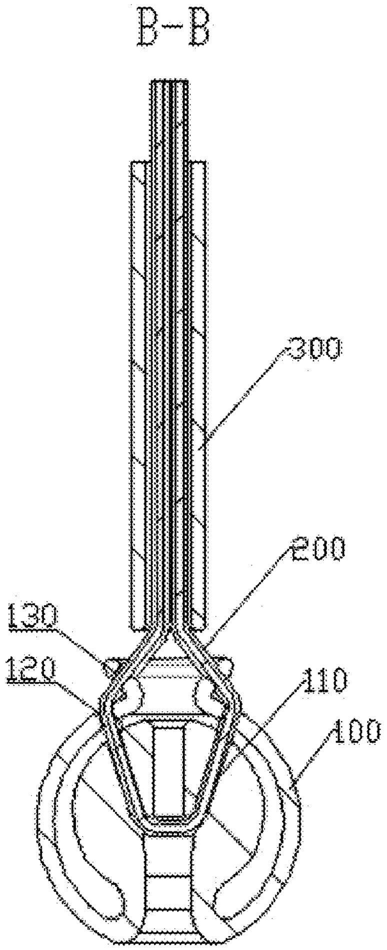
FIG. 5 shows a cross-sectional diagram taken along line B-B of FIG. 4.
Figure 6:
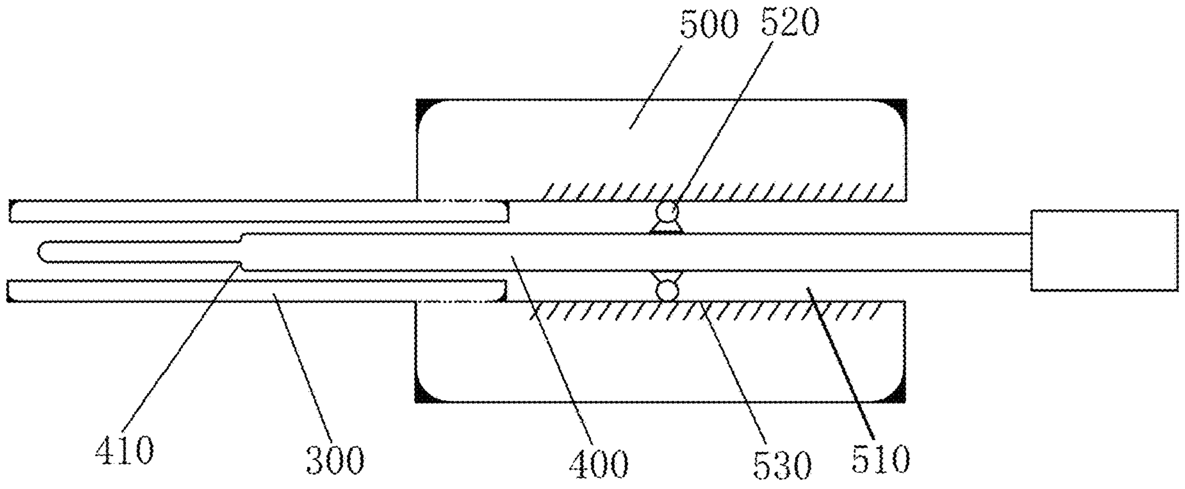
FIG. 6 shows a schematic structural diagram of a pulley and a chute.

Referring to FIGS. 2 to 4, the head end of the suture cannula 100 retracts into the suture cannula 100. The side of the retracted head end of the suture cannula 100 is provided with a first wire passing hole 110, and the pulling wire 200 penetrates into the first wire passing hole 100, forming an "expansion fuse" structure. Two second wire passing holes 120 are symmetrically provided at the tail side of the suture cannula 100. Both ends of the pulling wire 200 located in the suture cannula 100 pass out of the suture cannula 100 from the second wire passing holes 120, respectively, to form a group of symmetrical "locking rings". Two third wire passing holes 130 are provided at the side of the suture cannula 100. The third wire passing holes 130 are located at the side of the second wire passing hole 120 close to the outer tube 300. Both ends of the pulling wire 200 penetrate into the suture cannula 100 from the third wire passing holes 130 at the same side, respectively, and finally pass out of the end of the suture cannula 100, forming a locking structure. The pulling wire 200 between the second wire passing hole 120 and the third wire passing hole 130 is located outside the suture cannula 100.

In this embodiment, when the anchor is implanted, the pulling wire 200 and the inserter 400 move backward at the same time, thereby generating a backward pulling force. Under the action of the pulling force, because the pulling wire 200 passes through the side of the retracted head end of the suture cannula 100, the head end of the suture cannula 100 is pulled to move to its tail, and the head end of the suture cannula 100 is stacked from a single-layer structure to a double-layer structure. During the deformation process of the suture cannula 100, the outer tube 300 is always relatively fixed. The end of the outer tube 300 close to the suture cannula 100 can limit the continuous movement of the suture cannula 100, so that the force acting on the suture cannula 100 by the pulling wire 200 is converted into the deformation amount of the suture cannula 100.

When the suture cannula 100 starts to expand, the Poisson's ratio at the head end of the suture cannula 100 is maximal due to the stacking effect of the suture cannula 100 at this time. The side of the suture cannula 100 between the second wire passing hole 120 and the third wire passing hole 130 is only squeezed by movement and limit, so that the deformation at this point is only compression deformation, and the deformation is not obvious. After the expansion of the suture cannula 100 is completed, the displacement of the suture cannula 100 stops at the end of the outer tube 300 close to the suture cannula 100. As the suture cannula 100 at the second wire passing hole 120 and the third wire passing hole 130 is deformed, an annular limiting structure is formed. A trumpet-shaped structure is formed at the tail of the suture cannula 100. Under the action of friction resistance, the annular limiting structure of the suture cannula 100 limits the movement of the head end of the suture cannula 100 in the forward and backward directions, that is, at this time, the suture cannula 100 cannot move in the bone tissue along its length direction, thus completing the locking action.

With continued reference to FIGS. 3 and 4, the end of the pulling wire 200 at the head end of the suture cannula 100 pulls a part of the material of the head of the anchor into the suture cannula 100, forming an approximately spherical inner core. At this time, the suture cannula 100 forms a double-layer structure of an inner core and an outer shell. The annular limiting structure of the suture cannula 100 limits the inner core and the outer shell of the suture cannula 100 into a pocket shape. At this time, the suture cannula 100 between the second wire passing hole 120 and the third wire passing hole 130 is deformed into a similar pocket buckle structure due to the pulling force of the pulling wire 200.

In this embodiment, when the device works, the anchor is inserted after drilling holes on the surface of the bone tissue, and then the anchor is inserted to an appropriate depth. Then, the suture cannula 100 is pushed out of the outer tube 300 by the inserter 400, and then the pulling wire 200 and the inserter 400 are pulled out. At this time, the head end of the suture cannula 100 retracts inward and expands into a spherical shape. The diameter of the suture cannula 100 is greatly increased. The expanded suture cannula 100 squeezes the surrounding bone tissue. Then, the outer tube 300 is pulled out to separate the outer tube 300 from the suture cannula 100. The outer tube 300 and the inserter 400 are recovered, so that the suture cannula 100 is fixed in the bone tunnel. When the suture cannula 100 bears the axial pull-out load, the cortical layer of the bone will generate the bearing reaction opposite to the direction of the pulling force. At this time, the cancellous bone will also pressurize the suture cannula 100 to generate the contact pressure, so that the suture cannula 100 can stay firmly in the original position.

Embodiment 2

Referring to FIG. 1 to FIG. 5, the all-suture anchor provided in this embodiment is an improvement of some structures based on Embodiment 1 described above. Compared with the all-suture anchor provided in Embodiment 1 described above, the specific improvement of this embodiment is as follows.

In the all-suture anchor provided in this embodiment, the distal ends of the outer tube 300 and the inserter 400 are both connected with the same handle 500. The through hole 510 goes through the inside of the handle 500, and the outer surface of the outer tube 300 is fixedly connected with the side of the through hole 510. The inserter 400 goes through the handle 500 through the through hole 510. A pulley 520 is mounted at the side of the inserter 400 located in the handle 500. A chute 530 is provided in the handle 500, and the pulley 520 is only movable along the chute 530 in the handle 500.

In this embodiment, the displacement action and the connection relationship between the outer tube 300 and the inserter 400 are realized by the handle 500. When the suture cannula 100 needs to be knotted, the movement of the handle 500 is restricted by holding the handle 500 by hands. Since the outer tube 300 is fixedly connected with the handle 500, the handle 500 and the outer tube 300 can remain relatively stationary. Because the movement of the inserter 400 is restricted by the pulley 520 and the chute 530, the inserter 400 can only reciprocate linearly along the length direction of the chute 530, which can avoid the relative rotation of the inserter 400 and the outer tube 300 that will affect knotting of the suture cannula 100. On the contrary, the suture cannula 100 can complete the knotting process by the relative movement between the inserter 400 and the outer tube 300.

Embodiment 3

Referring to FIG. 1 to FIG. 5, this embodiment further provides an implantable device 1000, comprising the all-suture anchor described in Embodiment 1 and Embodiment 2 described above.

In the description of this specification, the description referring to the terms "one embodiment", "some embodiments", "examples", "specific examples" or "some examples" means that the specific features, structures, materials or characteristics described in connection with this embodiment or example are included in at least one embodiment or example of the present disclosure. In this specification, the schematic expressions of the above terms do not necessarily refer to the same embodiment or example. Further, the specific features, structures, materials or characteristics described may be combined in any one or more embodiments or examples in a suitable manner. In addition, those skilled in the art can incorporate and combine different embodiments or examples and features of different embodiments or examples described in this specification without contradicting each other.

Although the embodiments of the present disclosure have been shown and described above, it is to be understood that the above embodiments are exemplary and should not be construed as limiting the present disclosure. Those skilled in the art can make changes, modifications, substitutions and variations to the above embodiments within the scope of the present disclosure.

What is claimed is:

1. An all-suture anchor, comprising: a suture cannula, a pulling wire, an outer tube and an inserter, wherein the suture cannula is in interference fit with an inner wall of the outer tube, the pulling wire goes through the suture cannula, the pulling wire wraps around the inserter, the suture cannula and the outer tube are both in plug-in fit with the inserter, both ends of the pulling wire pass through the suture cannula, respectively, and pass out of one end of the outer tube far from the suture cannula, the inserter is configured to push the suture cannula out of the outer tube, and the pulling wire is configured to pull the suture cannula pushed out of the outer tube, so that the suture cannula retracts, stacks and expands.

2. The all-suture anchor according to claim 1, wherein a head end of the suture cannula retracts into the suture cannula, a side of the retracted head end of the suture cannula is provided with a first wire passing hole, and the pulling wire penetrates into the first wire passing hole.

3. The all-suture anchor according to claim 1, wherein two second wire passing holes and two third wire passing holes are symmetrically provided at a side of the suture cannula, the two third wire passing holes are located at a side of the two second wire passing holes close to the outer tube, and the pulling wire in the suture cannula is capable of passing out of the suture cannula from the two second wire passing holes, and then penetrates into the suture cannula from the corresponding two third wire passing holes.

4. The all-suture anchor according to claim 1, wherein the suture cannula has a hollow woven structure.

5. The all-suture anchor according to claim 1, wherein the inserter is provided with a shoulder-shaped sinking platform, and the shoulder-shaped sinking platform is configured to be in contact with a tail of the suture cannula to limit the detachment of the suture cannula.

6. The all-suture anchor according to claim 1, wherein the outer tube and the inserter are made of SUS304 medical stainless steel.

7. The all-suture anchor according to claim 1, wherein ends of the outer tube and the inserter far from the suture cannula are both connected with the same handle, a through hole goes through the inside of the handle, and the outer surface of the outer tube is fixedly connected with the side of the through hole.

8. The all-suture anchor according to claim 7, wherein the inserter goes through the handle through the through hole, a pulley is mounted at the side of the inserter located in the handle, a chute is provided in the handle, and the pulley is only movable along the chute in the handle.

9. An implantable device, comprising the all-suture anchor according to claim 1.

* * * * *